(12) United States Patent
Shin et al.

(10) Patent No.: US 9,920,290 B2
(45) Date of Patent: Mar. 20, 2018

(54) CONTINUOUS FERMENTATION APPARATUS AND MULTI-STEP CONTINUOUS FERMENTATION PROCESS USING THE SAME

(71) Applicants: BIOL SYSTEMS CO., LTD., Jeollanam-do (KR); DAEWOO SHIPBUILDING & MARINE ENGINEERING CO., LTD., Seoul (KR)

(72) Inventors: Myung Kyo Shin, Jeollanam-do (KR); Jin Hyuk Shin, Jeollanam-do (KR); In Sik Kim, Seoul (KR); Dongjoong Im, Seoul (KR)

(73) Assignees: Biol Systems Co., Ltd., Jeollanam-do (KR); Daewoo Shipbuilding & Marine Engineering Co., Ltd., Seoul (KR)

( * ) Notice: Subject to any disclaimer, the term of this patent is extended or adjusted under 35 U.S.C. 154(b) by 472 days.

(21) Appl. No.: 14/905,873

(22) PCT Filed: Oct. 26, 2012

(86) PCT No.: PCT/KR2012/008897
§ 371 (c)(1),
(2) Date: Jan. 18, 2016

(87) PCT Pub. No.: WO2013/062372
PCT Pub. Date: May 2, 2013

(65) Prior Publication Data
US 2016/0152934 A1    Jun. 2, 2016

(30) Foreign Application Priority Data
Oct. 27, 2011 (KR) .......................... 10-2011-0110790

(51) Int. Cl.
*C12M 1/12* (2006.01)
*C12M 1/00* (2006.01)
(Continued)

(52) U.S. Cl.
CPC ............ *C12M 23/06* (2013.01); *C12M 21/12* (2013.01); *C12M 23/34* (2013.01); *C12M 23/58* (2013.01);
(Continued)

(58) Field of Classification Search
CPC ...... C12M 21/12; C12M 23/06; C12M 23/34; C12M 23/58; C12M 27/02; C12M 29/04; C12P 7/10; C12P 7/14; Y02E 50/16
See application file for complete search history.

(56) References Cited

U.S. PATENT DOCUMENTS 5,149,652 A * 9/1992 Seals ................. B01D 19/0047
                                                  261/DIG. 19
8,017,366 B1    9/2011 Schuh et al.
(Continued)

FOREIGN PATENT DOCUMENTS

| KR | 10-2001-0077869 A | 8/2001 |
|----|-------------------|--------|
| WO | WO 2008/105618 A1 | 9/2008 |
| WO | WO 2008/120644    | 10/2008 |

OTHER PUBLICATIONS

Int'l. Search Report of PCT/KR2012/008897 dated Mar. 18, 2013.

*Primary Examiner* — Nathan A Bowers
*Assistant Examiner* — Lydia Edwards
(74) *Attorney, Agent, or Firm* — Greer, Burns & Crain, Ltd.

(57) ABSTRACT

The present disclosure relates to a continuous fermentation apparatus and a multi-step continuous fermentation process using the same.

10 Claims, 7 Drawing Sheets

(51) Int. Cl.
*C12M 1/06* (2006.01)
*C12P 7/14* (2006.01)
*C12P 7/10* (2006.01)

(52) U.S. Cl.
CPC ............ *C12M 27/02* (2013.01); *C12M 29/04* (2013.01); *C12P 7/10* (2013.01); *C12P 7/14* (2013.01); *Y02E 50/16* (2013.01)

(56) References Cited

U.S. PATENT DOCUMENTS

| | | | |
|---|---|---|---|
| 2009/0137013 A1* | 5/2009 | Schmid | C12N 1/12 435/134 |
| 2010/0068791 A1 | 3/2010 | Merimon et al. | |
| 2010/0144017 A1 | 6/2010 | Shepherd | |
| 2013/0005011 A1* | 1/2013 | Bell | C12M 27/02 435/161 |

* cited by examiner

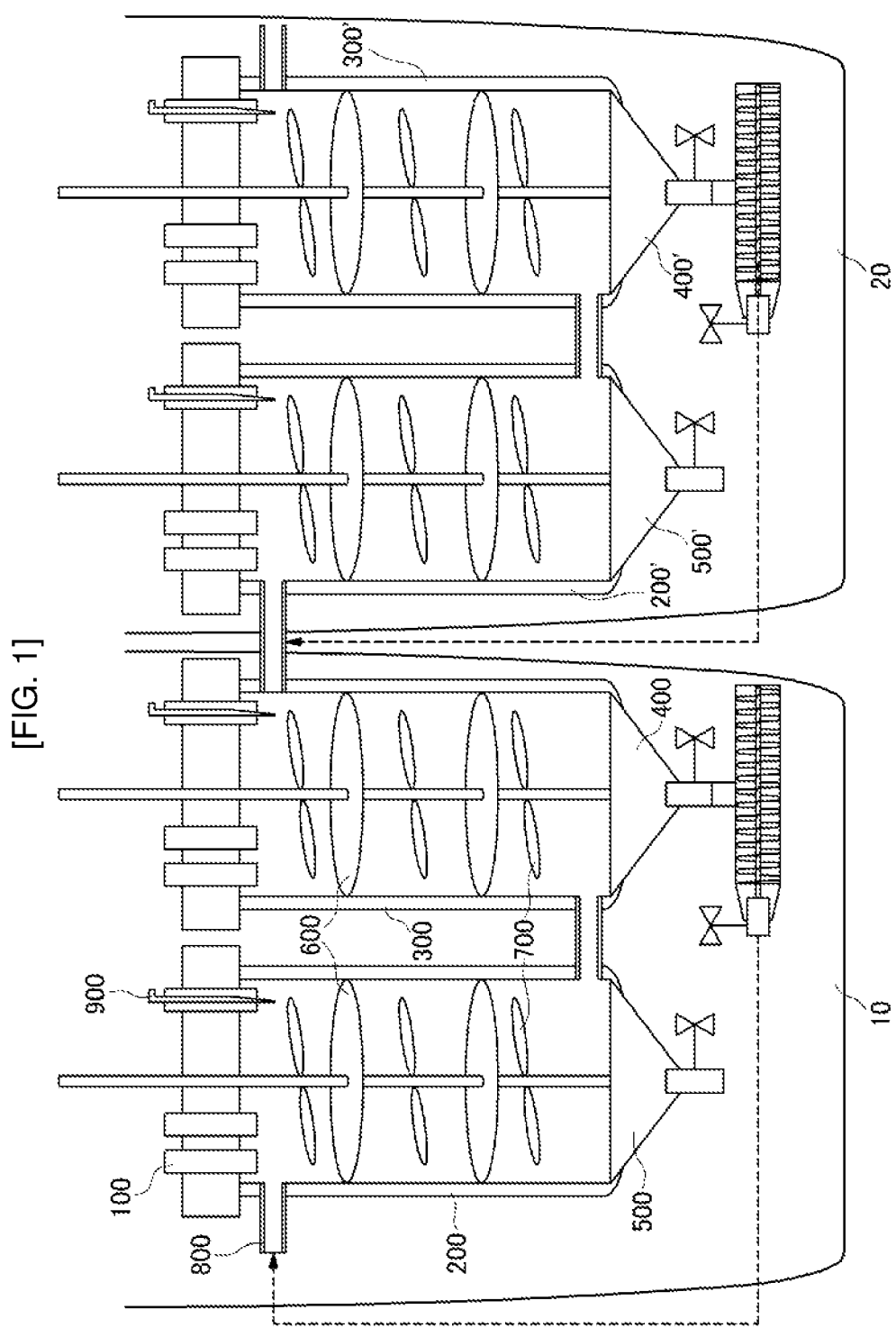

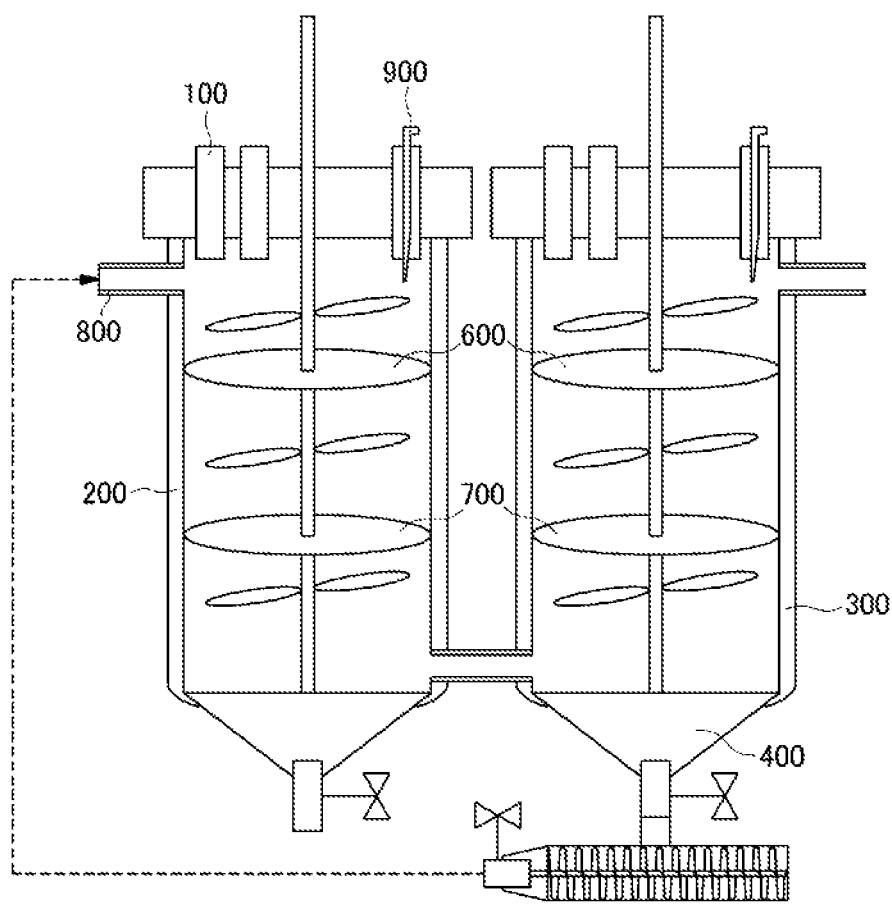
[Fig. 2]

[Fig. 3]
(a)
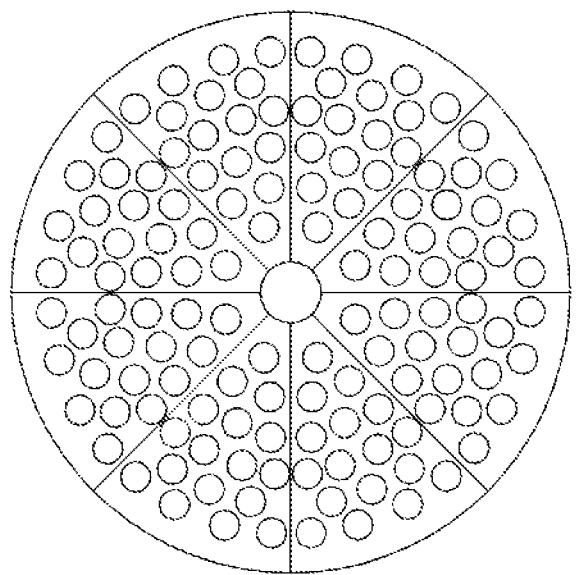
(b)
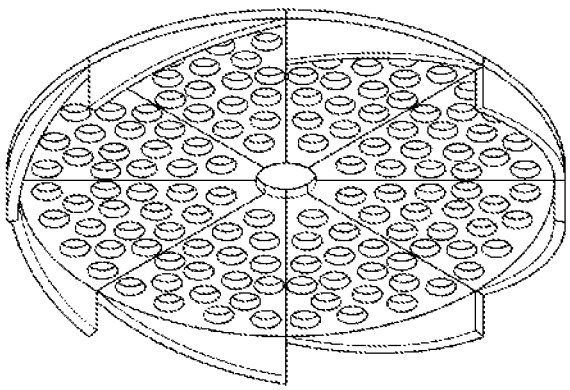

[Fig. 4]
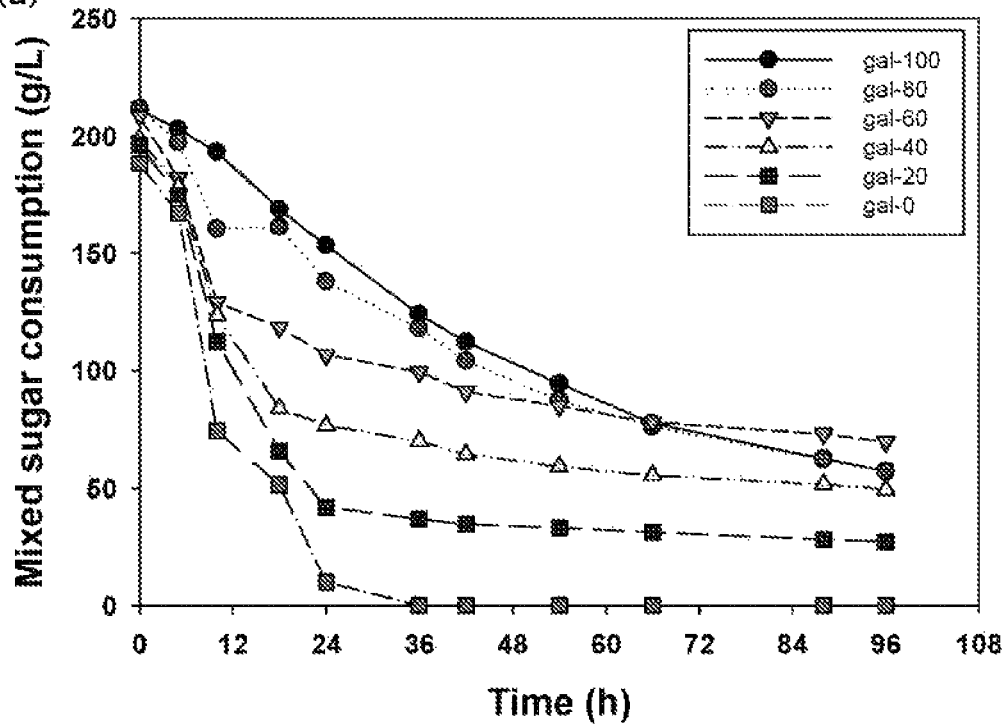
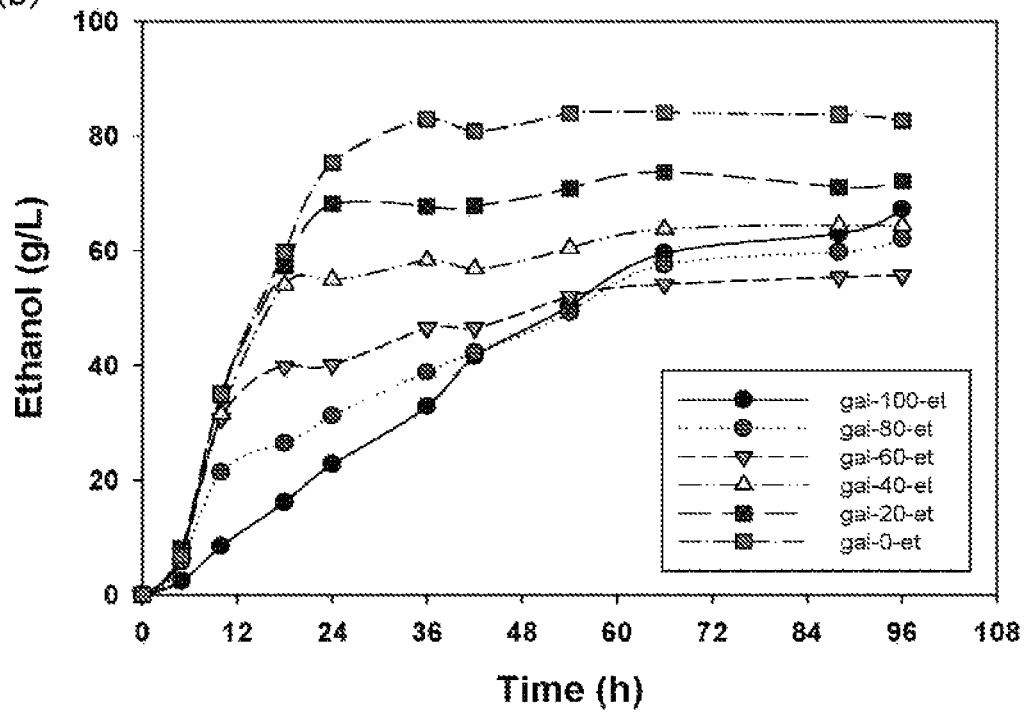

[Fig. 5]
(a)
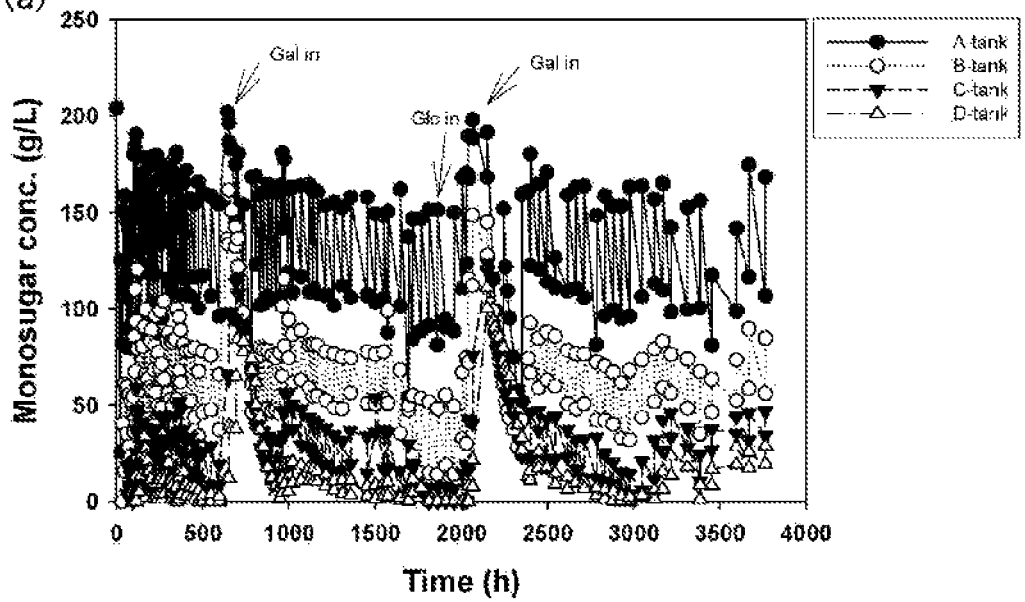
(b)
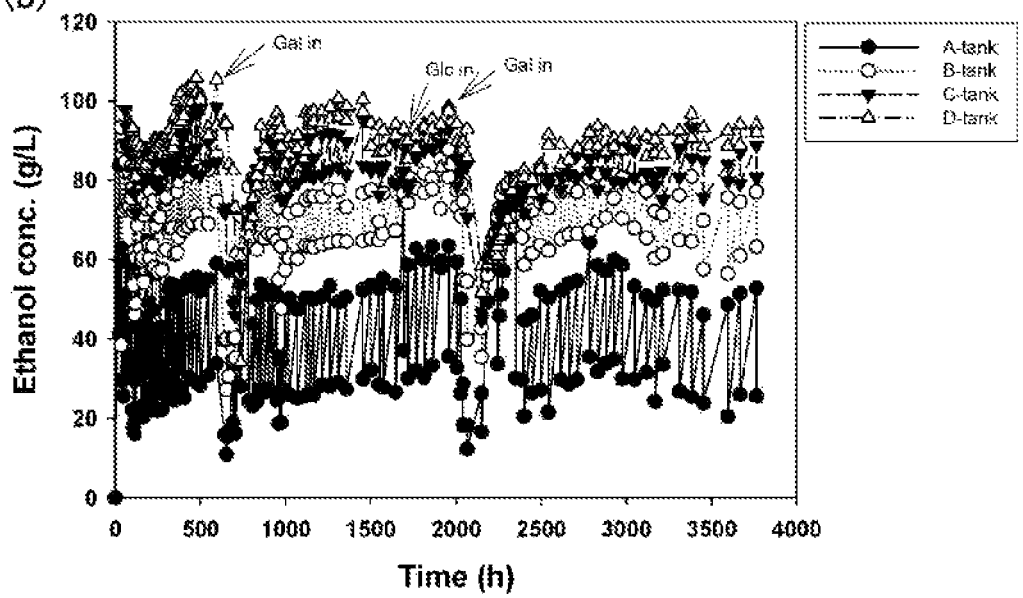

[FIG. 6]
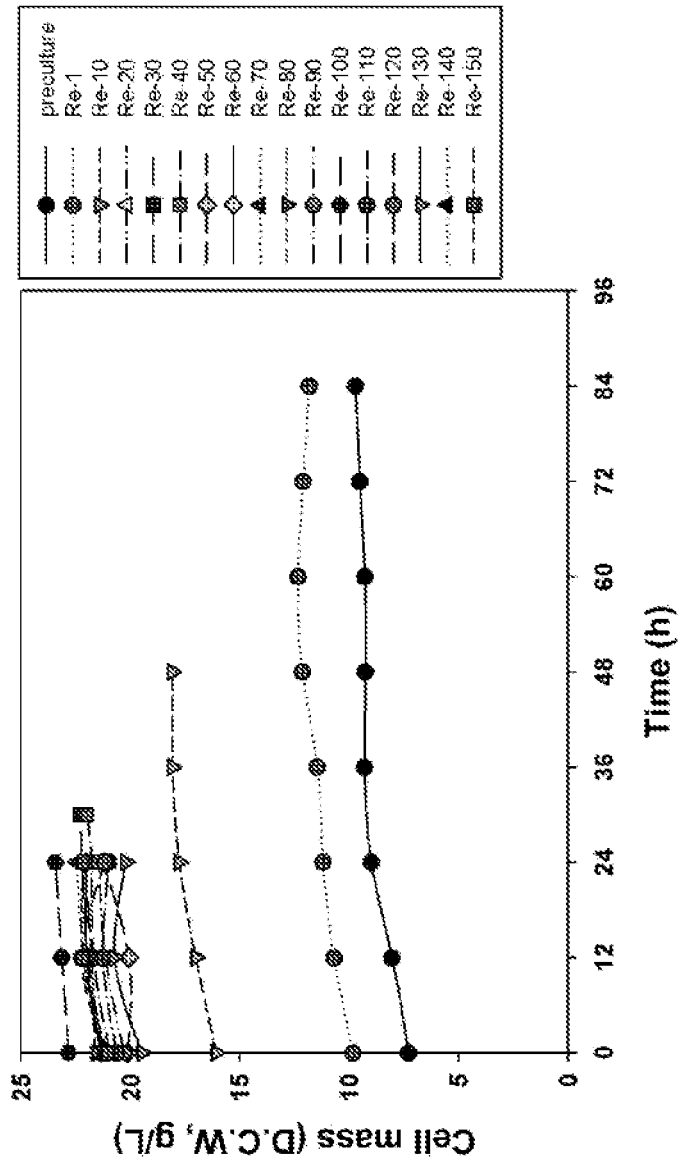

[Fig. 7]
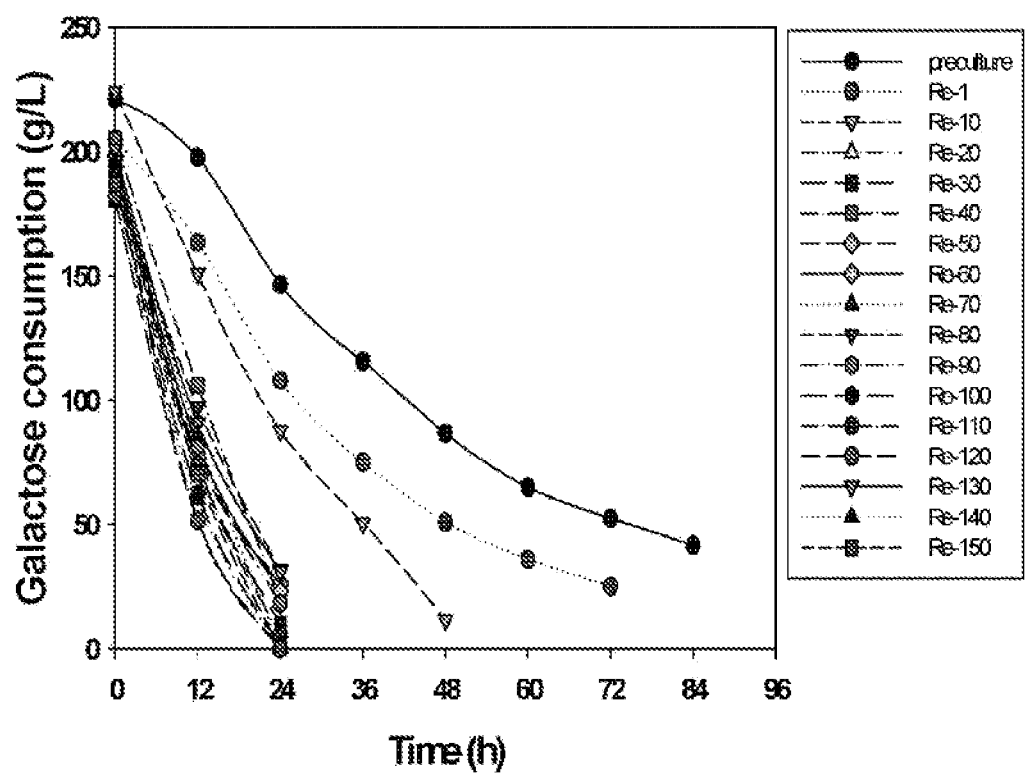

CONTINUOUS FERMENTATION APPARATUS AND MULTI-STEP CONTINUOUS FERMENTATION PROCESS USING THE SAME

TECHNICAL FIELD

The present disclosure relates to a continuous fermentation apparatus and a multi-step continuous fermentation process using the same.

BACKGROUND ART

Biomass is a general term to refer to all organic materials currently being used as energy sources including dedicated energy crops and trees, agricultural products and forage crops, agricultural wastes and residues, forest product wastes and wood chips, water plants, excretion of animals, industrial wastes including municipal wastes, and other renewable organic materials extracted from the above-described wastes. The biomass is a huge energy storage that keeps solar energy. If it is possible to effectively use the biomass, a current energy crisis caused by overuse of fossil fuels can be solved easily. Since the biomass is cultured to produce energy to be used as much as needed, it is possible to prevent excessive accumulation of carbon dioxide in the air. Therefore, it may be possible to solve global warming being currently brought up as a very serious problem.

Bioethanol as one of alternative energy sources using the biomass is extracted from plants such as sugar cane, corn, and the like and can be used as an automotive fuel in a combined manner with gasoline or solely. Therefore, the bioethanol has drawn attention as a representative renewable energy source together with biodiesel. Biomass ethanol is described in documents as follows: DiPardo, Journal of Outlook for Biomass Ethanol Production and Demand (EIA Forecasts), 2002; Sheehan, Biotechnology Progress, 15 8179, 1999; Martin, Enzyme Microbes Technology, 31 274, 2002; Greer, BioCycle, 61-65, April 2005; Lynd, Microbiology and Molecular Biology Reviews, 66 3, 506-577, 2002; and Lynd et al in "Consolidated Bioprocessing of Cellilosic Biomass: An Update," Current Opinion in Biotechnology, 16 577-583, 2005.

However, as the bioethanol has drawn attention as alternative energy, a demand for corn, sugar crane, and wheat as sources of the bioethanol has been sharply increased, which becomes a factor of a sharp rise in crop prices. Accordingly, a method of obtaining bioethanol from crops causes the above-mentioned problem of a sharp rise in crop prices and cannot avoid criticism that such crops should be supplied to many starving people as food. Therefore, a global bioethanol market has turned its attention from crops to wood. However, there is no way of making a breakthrough since the wood needs to go through a complicated process of removing lignin or the like.

Accordingly, recently, marine algae have drawn attention as a source of the bioethanol. Since the marine algae have a high growth rate, it is possible to mass-produce them without any fertilizer or agricultural water. Further, since the marine algae are rich in various sugar components and alginic acid, they are suitable to be converted into energy. Furthermore, the marine algae are about 1.5 to 2 times richer in carbohydrates than wood.

Moreover, since the marine algae have less dense structure than lignin, as compared with conventional biomass, it is relatively easy to perform saccharification on the marine algae, resulting in a great amount of output. Besides, since relatively abundant marine resources can be utilized, the marine algae have great potential.

DISCLOSURE OF INVENTION

Technical Problem

The present disclosure provides a continuous fermentation apparatus capable of collecting microbial cells and reusing them during a continuous fermentation process to produce biofuel and a multi-step continuous fermentation process using the same apparatus.

However, the problems to be solved by the present disclosure are not limited to the above description and other problems can be clearly understood by those skilled in the art from the following description.

Solution to Problem

In accordance with a first aspect of the present disclosure, there is provided a continuous fermentation apparatus including a source input unit; a fermentation unit including a downward fermentation tube and an upward fermentation tube; and a microbial cell collection unit formed on a lower part of the upward fermentation tube.

In accordance with an illustrative embodiment of the present disclosure, a plurality of fermentation units is included. If the source is sugar mixture, the number of fermentation unit may adjust according to the number of sugar contained in the sugar mixture In accordance with an illustrative embodiment of the present disclosure, the source includes, but is not limited to, one selected from the group consisting of marine algae, cellulosic biomass, and the combination thereof.

In accordance with an illustrative embodiment of the present disclosure, the source includes, but is not limited to, a sugar mixture selected from the group consisting of glucose, galactose, sucrose, xylose, and the combinations thereof.

In accordance with an illustrative embodiment of the present disclosure, continuous fermentation apparatus further includes, but is not limited to, a collection unit for collecting microbial cells and precipitates on a lower part of the downward fermentation tube.

In accordance with an illustrative embodiment of the present disclosure, the downward fermentation tube and the upward fermentation tube further includes, but is not limited to, an impeller and a screen.

In accordance with an illustrative embodiment of the present disclosure, the microbial cells collected by the microbial cell collection unit of the upward fermentation tube are supplied into the downward fermentation tube to be recycled, but is not limited thereto.

In accordance with a second aspect of the present disclosure, there is a provided a multi-step continuous fermentation process of sugar mixture using the continuous fermentation apparatus in the first aspect.

In accordance with an illustrative embodiment of the present disclosure, the process comprising the steps of supplying the sugar mixture into a source input unit; and fermenting the sugar mixture in a fermentation unit including a downward fermentation tube and an upward fermentation tube, but is not limited thereto.

In accordance with an illustrative embodiment of the present disclosure, microbial cells are collected from the upward fermentation tube and supplied into the downward fermentation tube to be recycled, but is not limited thereto.

In accordance with an illustrative embodiment of the present disclosure, the step of fermenting is carried out at least one time according to the number of sugar contained in the sugar mixture, but is not limited thereto.

Advantageous Effects of Invention

In accordance with the present disclosure, it is possible to continuously produce ethanol through continuous fermentation and the present disclosure can be applied to a fermentation process using sugar mixtures. Conventionally, sugars extracted from marine algae are not monosaccharides but sugar mixtures. Thus, even if a simple batch fermentation process and a conventional continuous fermentation process are carried out, a sugar shock occurs for a certain time, which results in an increase in a total fermentation time and also affects a fermentation yield. However, the present disclosure can solve such problems. Further, there is provided a separate harvesting unit at a lower part of a U-shaped tube, and, thus, it is possible to control respective strains, which maximizes the fermentation yield and makes it possible to perform the continuous fermentation process. Furthermore, microbial cells are collected and reused during a series of continuous fermentation processes, so that the total fermentation time can be reduced. Moreover, a specific sugar (glucose) from a saccharification liquid containing various sugars including the glucose is first fermented and the remaining sugars are successively fermented, so that it is possible to prevent a shock caused by a difference in metabolic pathways within a strain due to a difference in kinds of sugars.

BRIEF DESCRIPTION OF DRAWINGS

FIG. 1 is a schematic diagram of a continuous fermentation apparatus in accordance with an illustrative embodiment of the present disclosure; and FIG. 2 is a schematic view of a fermentation unit of a continuous fermentation apparatus in accordance with an illustrative embodiment of the present disclosure.

FIG. 3 is a schematic view of a screen of a continuous fermentation apparatus in accordance with an illustrative embodiment of the present disclosure.

FIG. 4 shows graphs of (a) sugar mixture consumption and (b) ethanol production under various ratio of galactose and glucose in accordance with example of the present disclosure.

FIG. 5 shows graphs of (a) mono-sugar consumption and (b) ethanol production in a continuous fermentation process in accordance with example of the present disclosure.

FIG. 6 is a graph showing time course of cell growth during the continuous fermentation process in accordance with example of the present disclosure.

FIG. 7 is a graph showing galactose consumption during the continuous fermentation process in accordance with example of the present disclosure.

BEST MODE FOR CARRYING OUT THE INVENTION

Hereinafter, embodiments of the present disclosure will be described in detail with reference to the accompanying drawings so that the present disclosure may be readily implemented by those skilled in the art. However, it is to be noted that the present disclosure is not limited to the embodiments but can be embodied in various other ways. In drawings, parts irrelevant to the description are omitted for the simplicity of explanation, and like reference numerals denote like parts through the whole document.

Hereinafter, embodiments of the present disclosure will be described in detail with reference to the accompanying drawings so that the present disclosure may be readily implemented by those skilled in the art. However, it is to be noted that the present disclosure is not limited to the embodiments but can be embodied in various other ways. In drawings, parts irrelevant to the description are omitted for the simplicity of explanation, and like reference numerals denote like parts through the whole document.

Through the whole document, the term "on" that is used to designate a position of one element with respect to another element includes both a case that the one element is adjacent to the another element and a case that any other element exists between these two elements.

Further, the term "comprises or includes" and/or "comprising or including" used in the document means that one or more other components, steps, operation and/or existence or addition of elements are not excluded in addition to the described components, steps, operation and/or elements unless context dictates otherwise. The term "about or approximately" or "substantially" are intended to have meanings close to numerical values or ranges specified with an allowable error and intended to prevent accurate or absolute numerical values disclosed for understanding of the present disclosure from being illegally or unfairly used by any unconscionable third party. Through the whole document, the term "step of" does not mean "step for".

Through the whole document, the term "combination of" included in Markush type description means mixture or combination of one or more components, steps, operations and/or elements selected from a group consisting of components, steps, operation and/or elements described in Markush type and thereby means that the disclosure includes one or more components, steps, operations and/or elements selected from the Markush group.

The present disclosure provides a column-type continuous fermentation apparatus including at least one fermentation unit including U-shaped downward and upward fermentation tubes each formed by connecting cylindrical column straight tubes are successively connected to one another. Each U-shaped downward and upward fermentation tubes may include a screw that pushes downwards and a screw that pushes upwards on its right and left sides, respectively. At a lower part of respective U-shaped upward fermentation tubes, a separated microbial cell collection unit capable of separating cells may be provided, and the cells may be recycled. In accordance with an illustrative embodiment, if a sugar mixture containing both galactose and glucose is fermented, yeast first consumes the glucose and then the galactose. In this case, a galactose shock may occur and the fermentation may be delayed.

In accordance with an illustrative embodiment of the present disclosure, during a first-step continuous fermentation process in a first fermentation unit, glucose is first fermented and then microbial cells are separately collected. A culture medium in which a glucose is removed and only the galactose remains is transferred to second fermentation unit including U-shaped downward and upward fermentation tubes. Microbial cells collected in the U-shaped upward fermentation tube of the first fermentation unit are supplied to a U-shaped downward fermentation tube of the first fermentation unit to ferment glutose. In the same manner, fermented broth in which most of glucose is consumed is transferred to the U-shaped downward and upward fermentation tubes of the second fermentation unit, and, thus, the yeast can consume only the galactose without a shock. After the fermentation, microbial cells collected by a microbial cell collection unit provided at a lower part of the upward fermentation tube of the second fermentation unit are supplied to the inlet of the downward fermentation tube of the second fermentation unit, so that it is possible to suppress a delay in fermentation of the sugar mixture and also possible to reduce a total time for a continuous fermentation process. This can be applied to other sugar mixtures.

The above-described fermentation process is performed to convert monosaccharides remaining after saccharification into biofuel by fermenting the monosaccharides with microorganisms such as yeast.

The microorganisms for fermentation may include any one selected from the group consisting of, but not limited to, *Brettanomyces bruxellensis, Saccharomyces pastorianus, Saccharomyces cerevisiae, Sarcina ventriculi, Kluyveromyces fragilis, Zymomonas mobilis, Kluyveromyces marxianus IMB3, Brettanomyces custersii, Clostridium acetobutylicum, Clostridium beijerinckii, Clostridium aurantibutylicum, Clostridium tetanomorphum*, variants thereof, and combinations thereof.

As fermentation conditions, a temperature of a fermentation unit is maintained in a range of from about 20° C. to about 70° C. and may be maintained to be lower than about 45° C., for example, lower than about 42° C. (from about 34° C. to about 38° C., or about 37° C.). In some cases, the fermentation unit may be maintained at a temperature higher than about 5° C., for example, a temperature higher than about 15° C.

Hereinafter, a continuous fermentation apparatus in accordance with an illustrative embodiment will be explained in detail with reference to FIGS. 1 and 2. However, the present disclosure is not limited thereto.

Referring to FIGS. 1 and 2, a continuous fermentation apparatus in accordance with an illustrative embodiment includes a source input unit 100, a first fermentation unit 10 including a downward fermentation tube 200 and an upward fermentation tube 300, a second fermentation unit including a downward fermentation tube 200' and an upward fermentation tube 300' and a microbial cell collection unit 400, 400'.

The source input unit 100 as a apparatus for controlling a speed of a pre-fermentation process is configured to supply a source. For example, the source input unit 100 may supply the source with certain flow rate per hour. The source may include, but is not limited to, marine algae including macro-algae and micro-algae and terrestrial cellulosic biomass. For example, the source may include, but is not limited to, sugar mixture selected from the group consisting of glucose, galactose, sucrose, xylose, and the combinations thereof.

The downward fermentation tube 200, 200' may include a screw-type impeller 700 for preventing microbial cells from sedimentation, a driving unit at an upper part thereof, a carbon dioxide outlet 900 for discharging carbon dioxide generated during fermentation, and a screen 600 for preventing upper and lower solutions within the fermentation tube from being mixed with each other. The screen 600 may be in form of porous plate, and blades in shape of Right-angled triangle may be formed on surface of the screen 600. The screen 600 may prevent the microbial cells from sedimentation during rotation in the downward fermentation tube to prevent loss of the microbial cells. The porous plate has pores having size from about 0.1 mm to about 10 mm, and the pores are formed in shape which upper part is narrow and lower part is broad.

The downward fermentation tube 200, 200' may include a collection unit 500, 500' for collecting microbial cells and precipitates on a lower part of the downward fermentation tube.

The upward fermentation tube 300, 300' may include a screw-type impeller 700, a driving unit at an upper part thereof, a carbon dioxide outlet 900 for discharging carbon dioxide generated during fermentation, and a screen 600 for preventing upper and lower solutions within the fermentation tube from being mixed with each other. The screen 600 may be in form of porous plate, in particular may be use the porous plate identical with that of the downward fermentation tube. Blades in shape of Right-angled triangle may be formed on surface of the screen 600, and pores of the porous plate are range of from about 0.1 mm to about 10 mm. The screen 600 may be used as overturned form with respect to that of the downward fermentation tube. The screen 600 may prevent a rise of the microbial cells.

At a lower part of the upward fermentation tube 300, 300' the microbial cell collection unit 400, 400' may be provided. A guard and a screen 600 for suppressing a rise of microbial cells may be provided within the fermentation tube. Collected microbial cells can be supplied into a microbial cell input 800, and recycled in the downward fermentation tube 200, 200'. Therefore, the present disclosure can provide a recycling system for circulating collected microbial cells in a fermentation process.

There may be provided a apparatus for suppressing a rise of microbial cells in an upward fermentation unit equipped with the microbial cell collection unit 400, 400'.

The present disclosure can be applied to fermentation of a sugar mixture by connecting the same fermentation unit systems depending on the number of sugar included in the sugar mixture.

MODE FOR THE INVENTION

Example

Example 1

A sugar mixture including glucose and galactose was fermented using *B. custersii* in a continuous fermentation apparatus of FIG. 1.

FIG. 4 shows graphs of (a) sugar mixture consumption and (b) ethanol production under various ratio of galactose and glucose with 1% N-source. It can be confirmed that fermentation rate of the sugar mixture are decreased.

FIG. 5 shows graphs of (a) mono-sugar consumption and (b) ethanol production using 20% sugar with 1% N-source. Temporary fermentation delay was occurred due to conversion of monosugar of sugar mixture as carbon source during a continuous fermentation process using recycled microbial cells, but fermentation rate is shortly recovered.

FIG. 6 is a graph showing time course of cell growth during the continuous fermentation process under 200 g/L galactose with 1% N-source, and FIG. 7 is a graph showing galactose consumption by Brettanomyces custersii during the continuous fermentation process depending on the recycle number of microbial cells. As the recycle number of microbial cells is increased, a cell mass is increased and sugar consumption is rapidly decreased, and thus a conversion rate of fermentation is improved.

The above description of the present disclosure is provided for the purpose of illustration, and it would be understood by those skilled in the art that various changes and modifications may be made without changing technical conception and essential features of the present disclosure. Thus, it is clear that the above-described embodiments are illustrative in all aspects and do not limit the present disclosure. For example, each component described to be of a single type can be implemented in a distributed manner. Likewise, components described to be distributed can be implemented in a combined manner.

The scope of the present disclosure is defined by the following claims rather than by the detailed description of the embodiment. It shall be understood that all modifications and embodiments conceived from the meaning and scope of the claims and their equivalents are included in the scope of the present disclosure.

EXPLANATION OF CODES

10: first fermentation unit
20: second fermentation unit
100: Input unit
200, 200': Downward fermentation tube
300, 300': Upward fermentation tube
400, 400': Microbial cell collection unit
500, 500': collection unit
600: screen
700: impeller
800: microbial cell input
900: carbon dioxide outlet

The invention claimed is:

1. An apparatus for performing a continuous fermentation process of a sugar mixture, the apparatus comprising:
   a U-shaped fermentation unit including a downward fermentation tube, an upward fermentation tube, and a channel connecting the downward fermentation tube and the upward fermentation tube;
   a source input unit provided at an upper part of the downward fermentation tube configured to supply the sugar mixture into the downward fermentation tube;
   the channel connecting a lower part of the downward fermentation tube with a lower part of the upward fermentation tube and configured to pass the sugar mixture fermented in the downward fermentation tube into the lower part of the upward fermentation tube; and
   a microbial cell collection unit formed on the lower part of the upward fermentation tube configured to collect microbial cells from the sugar mixture;
   wherein the sugar mixture flows continuously downwardly through the downward fermentation tube from the source input unit and upwardly through the upward fermentation tube from the connecting channel.

2. The apparatus of claim 1, further comprising at least one additional U-shaped fermentation unit operatively connected to the U-shaped fermentation unit.

3. The apparatus of claim 1, wherein the sugar mixture is extracted from a source selected from the group consisting of marine algae, cellulosic biomass, and the combination thereof.

4. The apparatus of claim 1, wherein the sugar mixture is selected from the group consisting of glucose, galactose, sucrose, xylose, and the combinations thereof.

5. The apparatus of claim 1, further including a collection unit configured to collect microbial cells and precipitates on the lower part of the downward fermentation tube.

6. The apparatus of claim 1, wherein the downward fermentation tube and the upward fermentation tube further includes at least one impeller and at least one screen.

7. The apparatus of claim 2, wherein the microbial cells collected by the microbial cell collection unit of the upward fermentation tube are supplied into the downward fermentation tube to be recycled.

8. A continuous fermentation method for fermenting sugar mixture using an apparatus as claimed in any one of claims 1 to 7, the method comprising;
   supplying the sugar mixture into the source input unit of the downward fermentation tube; and
   impelling the sugar mixture downwardly through the downward fermentation tube and upwardly through the upward fermentation tube.

9. The method of claim 8, wherein microbial cells are collected from the upward fermentation tube and supplied into the downward fermentation tube to be recycled.

10. The method of claim 8, wherein the step of impelling the sugar mixture is repeated at least one more time according to the amount of sugar contained in the sugar mixture.

* * * * *